United States Patent [19]

DuBe et al.

[11] Patent Number: 4,988,294
[45] Date of Patent: Jan. 29, 1991

[54] DETACHABLE ABRASIVE DISK

[75] Inventors: D. Robert DuBe; Lawrence A. May, both of St. Paul, Minn.

[73] Assignee: Minnesota Mining and Manufacturing Company, St. Paul, Minn.

[21] Appl. No.: 815,219

[22] Filed: Dec. 31, 1985

Related U.S. Application Data

[63] Continuation of Ser. No. 170,561, Jul. 21, 1980, Pat. No. 4,601,661.

[51] Int. Cl.$^5$ ............................................. A61C 3/06
[52] U.S. Cl. ................................................... 433/134
[58] Field of Search ........................... 433/134, 166

[56] References Cited

U.S. PATENT DOCUMENTS

| | | | |
|---|---|---|---|
| 302,952 | 8/1884 | Smith . | |
| 336,695 | 2/1886 | Byers . | |
| 456,208 | 7/1891 | Schycker | 433/134 |
| 478,881 | 7/1892 | Moore | 433/134 |
| 1,314,125 | 8/1919 | Burlew | 433/134 |
| 1,355,888 | 8/1919 | Burlew . | |
| 1,506,078 | 8/1924 | Parks . | |
| 1,599,298 | 9/1926 | Stoloff . | |
| 1,786,320 | 12/1930 | Stratford . | |
| 2,991,596 | 7/1961 | Walters | 51/194 |
| 2,996,851 | 8/1961 | Gianatasio . | |
| 3,239,971 | 3/1966 | Freerks | 51/389 |
| 3,307,300 | 3/1967 | Field | 51/389 |
| 3,340,652 | 9/1967 | Purcell, Jr. | 51/376 |
| 3,514,116 | 5/1970 | Brinkman | 279/2 |
| 3,562,968 | 2/1971 | Johnson | 51/389 |
| 3,667,169 | 6/1972 | MacKay, Jr. | 51/379 |
| 3,789,462 | 2/1974 | Reich | 433/166 |
| 3,858,368 | 1/1975 | Cocherell | 433/166 |
| 3,883,998 | 5/1975 | Dosser . | |
| 3,894,339 | 7/1975 | Manzi | 32/59 |
| 4,055,897 | 11/1977 | Brix | 32/59 |
| 4,185,388 | 1/1980 | Jarby | 433/125 |

FOREIGN PATENT DOCUMENTS

| | | |
|---|---|---|
| 1818472 | 9/1960 | Fed. Rep. of Germany . |
| 1930881 | 3/1962 | Fed. Rep. of Germany . |
| 1978301 | 10/1962 | Fed. Rep. of Germany . |
| 2710826 | 9/1977 | Fed. Rep. of Germany . |
| 5117656 | 7/1974 | Japan . |
| 53122574 | 3/1977 | Japan . |
| 5563426 | 10/1978 | Japan . |

OTHER PUBLICATIONS

Dental Catalogue, "Veratex", Winter 1976, p. 62, Vertex Corp., 18610 Fitzpatrick, Detroit, Mich. 48228.
"Polyrapid", Rotary Bristle Brushes (set of 4), undated.
Polyrapid S.A. Catalog, undated.
Weiler Bursten GmbH Catalog page, undated.
Der Grobe Brodhaus, p. 667 (1933).
Hutte, Taschenbuch Furbetriebsingenieure, vol. 1, pp. 86, 87 and 574–577 (1964) w/translation.
Machinery's Handbook, pp. 1982, 1983 and 1986 (1979).
Leugger Lexikon Der Technik, vol. 3, p. 593 (1961) w/translation.

Primary Examiner—Cary E. Stone
Attorney, Agent, or Firm—Donald M. Sell; Walter N. Kirn; David R. Cleveland

[57] ABSTRACT

Dental mandrels, circular in cross-section, and detachable abrasive disks useful in confined areas of the mouth, in which the disk can be mounted on and demounted from the mandrel using finger pressure, and the disk can optionally be rotated relative to the mandrel when the mandrel is at rest, but the disk is gripped sufficiently firmly when the mandrel is spinning that no slippage of the disk is apparent under dental grinding conditions.

5 Claims, 2 Drawing Sheets

DETACHABLE ABRASIVE DISK

This is a continuation of Ser. No. 170,561 filed July 21, 1980, now U.S. Pat. No. 4,601,661.

TECHNICAL FIELD

This invention relates to abrading devices and processes for their utilization. In one aspect, the present invention relates to dental tools and processes useful for shaping and polishing various surfaces such as dental composite restorative resins. In another aspect, the present invention relates to mandrels useful in powered rotary dental tools. In yet a further aspect, the present invention relates to circular coated abrasive disks which can be detachably mounted on such mandrels.

BACKGROUND ART

Dentists frequently carry out shaping and polishing of materials such as dental restorative resins using detachable abrasive disks which are mounted on a mandrel driven by a powered rotary dental tool. Two commercially available detachable disk and mandrel combinations are commonly used, these two combinations ordinarily being referred to as the "Moore's Brass Center Disk and Mandrel" (apparently named after the principal manufacturer, E. C. Moore Co., Inc.) and the "Pinhole" disk and mandrel.

The "Moore" type brass center disk and mandrel employs a circular abrasive disk having a central hub with a square central hole. The hub is generally made by inserting a cylindrical brass eyelet into a hole in the abrasive disk and staking the brass eyelet using a suitable punch. The staked eyelet serves to reinforce the disk and provide a rotationally locked fastening means between disk and mandrel. The disk is mounted on a live mandrel having an end or arbor which is square in cross-section, axially bisected by a slot, and shaped and sized to dimensions sufficient to lockingly engage the square hole in the disk hub. "Moore" brass center disks and mandrels are well known to dentists and are illustrated in publications such as "Moore's Disk Sample Chart" (manufacturer's literature). A "Moore" type brass center disk hub is also shown in U.S. Pat. Nos. 478,881 and 4,055,897.

"Moore" brass center type disks and mandrels are widely used by dentists because disk replacement is relatively easy. However, the disk must be oriented so that the square hub in the disk is aligned with the square end on the mandrel in order to attach the disk to the mandrel. Also, a "Moore" brass center disk and mandrel must be used with care, as the end of the mandrel projects beyond the face of the mounted disk, and this projecting end has aggressive edges. If the rotating projecting end of the mandrel inadvertently strikes a dental restoration, a black mark can be left on the surface of the restoration. Also, the impact of the rotating projecting end against a dental restoration or tooth surface can cause objectionable patient pain and sensation. In addition, the edge of the disk hub can inadvertently strike a dental restoration or tooth surface even if the end of the mandrel does not do so, and the hub can thereby mark the surface of the restoration or cause patient pain.

Another drawback to the "Moore" brass center disk and mandrel is that the physical dimensions of the hub constrain the ultimate minimum useful disk diameter. The square hole in the hub is approximately 3 millimeters on each side, and the hub is generally 6 to 7 millimeters in diameter. Commercially available "Moore" type brass center disks are generally no smaller than about 13 millimeters diameter, and such disks are generally too large to be conveniently used in some closely confined dental work such as repair of cervical erosions, and Class I and Class II restorations of the occlusal anatomy of posterior teeth.

The pinhole disk and mandrel, the other commonly used detachable disk and mandrel combination, employs a disk having a central hole of approximately 1.7 millimeters diameter. No reinforcing hub is used in such a disk. The pinhole disk is mounted by placing the disk on the shaft of a truss-head or fillister-head machine screw which screw is then screwed into an axially threaded hole in the pinhole mandrel. The pinhole mandrel is provided with a shoulder against which the disk and machine screw bear. The binding action of the screw locks the disk in place. Pinhole disks and mandrels are also well known to dentists and are illustrated, for example, in U.S. Pat. Nos. 302,952, 336,695, and 1,506,078.

The pinhole disk and mandrel must also be used with care, as the protruding machine screw can accidentally strike the surface of a dental restoration or tooth, with attendant marking of the surface of the dental restoration and/or patient discomfort. An additional disadvantage of the pinhole disk and mandrel is that disk replacement is relatively cumbersome, requiring removal and rethreading of the machine screw each time a disk is replaced. Also, the ultimate minimum useful disk diameter for a pinhole disk and mandrel is constrained by the physical dimensions of the machine screw. Commercially available pinhole disks, like "Moore" brass center disks, are generally about 13 millimeters diameter or larger, and such pinhole disks are therefore too large to be used in some closely confined dental work such as repair of cervical erosions and Class I and Class II restorations of the occlusal anatomy of posterior teeth. Some pinhole disk manufacturers will supply custom made pinhole disks in diameters less than 13 mm for use by dentists who are willing to grind down the pinhole mandrel machine screw head to a smaller diameter. Disk replacement is still somewhat cumbersome with such a modified mandrel, and the disk may have a tendency to slip under load due to the reduced machine screw head size.

Other detachable abrasive disk and mandrel systems described for dental use are shown in U.S. Pat. No. 1,599,298 (in which a mandrel having a machine screw fastening means is provided with a cup shape locking screw having incorporated therein a helical locking spring) and U.S. Pat. No. 3,858,368 (in which a disk attached to a flexible sleeve is provided with a square axial hole in the sleeve, in order that the disk may be detachably mounted on an arbor having a square cross-section).

Also, in U.S. Pat. No. 3,789,462 there is shown a flexible dental polishing unit which is provided with an undercut indented bore having a non-circular cross-section, the polishing unit being mounted on a shaft having a non-circular cross-section corresponding to the bore of the polishing unit.

Other patents relating to detachable abrasive or polishing disks or mandrels are U.S. Pat. Nos. 1,786,320, 3,307,300, and 3,833,998. These patents describe detachable abrasive disks and mandrels useful for large scale polishing and abrasive equipment such as auto body polishers and disk sanders.

All of the above references specifically refer to the need for providing some positive, static locking means which would prevent rotation of the abrasive disk on the mandrel, whether the mandrel is in use (i.e. spinning) or merely at rest (i.e., not spinning). Locking means employed in the above references include disks having square or non-circular central holes mated with mandrels having a corresponding square or non-circular cross-section, as well as locking screws, springs, and the like. The use of such locking means requires care in alignment when the disk is placed on the mandrel. Also, locking means which project aggressively beyond the working face of the disk can be difficult to use in dental applications, because the locking means can strike the surface of a dental restoration or tooth during use. In addition, use of locking means which are square or non-circular in cross-section adds to the cost of manufacture of the disk and mandrel.

DISCLOSURE OF THE INVENTION

The present invention provides, in one aspect:
an abrading device, comprising:
(a) a circular abrasive disk, said disk having a central aperture and a grommet through said aperture, said grommet being firmly attached to said disk and having a circular hole whose axis is essentially perpendicular to said disk; and
(b) a rod-like mandrel having a driving end and a working end, said driving end being adapted to be mounted in a powered dental tool, said working end comprising:
  (i) a knob-like terminal portion having in axial cross-section a circular shape with a maximum diameter equal to or greater than the diameter of said circular hole in said grommet;
  (ii) a shoulder between said knob-like terminal portion and said driving end, said shoulder having in axial cross-section a minimum diameter greater than the diameter of said circular hole in said grommet; and
  (iii) means for providing dynamic driving engagement between said knob-like terminal portion and said grommet when said grommet is positioned around said knob-like terminal portion.

The present invention also provides new dental abrasive disks, new dental mandrels, and processes for shaping and polishing dental restorative resins in confined areas of the mouth.

BRIEF DESCRIPTION OF THE DRAWING

In the accompanying drawing.

DETAILED DESCRIPTION

Figure 1:
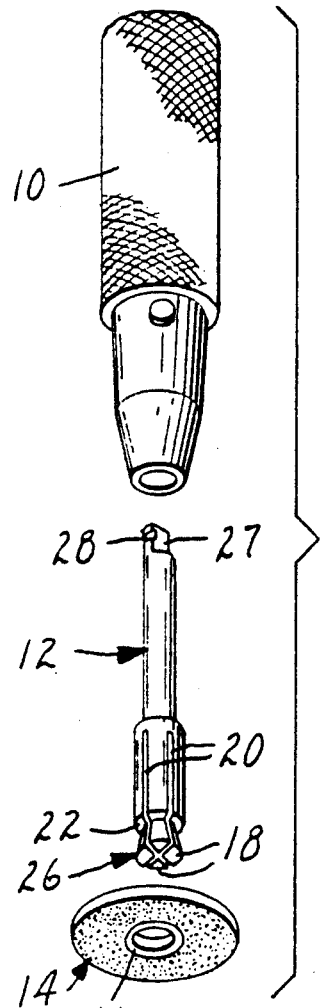
FIG. 1 is a perspective view showing an abrasive disk and mandrel of this invention mounted in a conventional powered rotary dental tool.

In the practice of the present invention, an abrasive disk having a grommet or hub provided with a round, axial hole is detachably mounted on a shouldered mandrel having a knob-like arbor, which arbor is round in cross-section, has means for providing dynamic driving engagement between the arbor and the abrasive disk, and is shaped or tapered to provide for easy mounting and demounting of the abrasive disk. The working end of the mandrel does not protrude excessively beyond the face of the mounted disk, and presents a low, non-aggressive profile having less tendency to strike the surface of a dental restoration or a patient's tooth than detachable dental abrasive disks and mandrels of the prior art. Also, the disk grommet is compact, does not occupy a large portion of the available abrasive disk working area, and has less tendency to strike the surface of a dental restoration or a patient's tooth than the hub of a "Moore" brass center disk (if an abrasive disk of this invention is compared to a "Moore" brass center disk of similar diameter). Due to the compact dimensions of the mandrel and grommet, the abrasive disks of this invention can be made in very small diameters (e.g. as low as about 6 mm), thereby enabling use of such disks in portions of the mouth not conveniently reached with detachable dental abrasive disks of the prior art.

In contrast to currently used detachable dental abrasive disks, positive static locking means between disk and mandrel (e.g., square or non-circular collet and mandrel, locking screws, etc. which lock the rotational position of the disk relative to the mandrel whether the mandrel is in use or at rest) are not used in this invention. When a disk of this invention is mounted on a mandrel of this invention, and the mandrel is at rest, the disk and mandrel are preferably in "static disengagement", that is, the disk preferably can be rotated with respect to the central axis of the mandrel with relative ease (e.g., by twisting, using finger pressure). When the disk and mandrel of this invention are rotated in a powered rotary dental tool, the disk and mandrel are in "dynamic driving engagement", that is, the arbor engages the grommet of the disk with sufficient firmness to enable ordinary dental grinding and polishing to be carried out without apparent slippage of the disk relative to the mandrel. Such dynamic driving engagement is provided in this invention in one embodiment by using a split arbor which expands against and grippingly engages the inner walls of the grommet (due to spring action of the arbor segments or centrifugal force acting upon those segments when the mandrel is rotated), and, in another embodiment, by using an unsplit arbor and a resilient, deformable rubber or plastic coupling means which frictionally engages the disk with sufficient firmness to prevent rotational slippage of the disk relative to the mandrel under dental grinding conditions. As used herein, "arbor" refers generally to the working end of the mandrels of this invention, and includes the knob-like terminal portion, shoulder, and any generally axial slot or slots in said working end.

Referring now to FIG. 1, there is shown a standard powered rotary dental tool or hand piece 10, adapted to rotationally drive a mandrel, designated generally by the numeral 12. Hidden from view is the driven end of mandrel 12, which is detachably coupled inside tool 10. At the working end of mandrel 12 is shown abrasive disk 14, being used to shape the surface of a restorative material on tooth 15. The abrasive disk backing is firmly fixed to central grommet 16. The grommet is detachably mounted on a split arbor or gudgeon at the working end of the mandrel. Removal and replacement of the abrasive disk on the mandrel is facilitated by slots 20 in the working end of mandrel 12, these slots allowing split segments 18 to compress sufficiently to allow attachment and removal of the abrasive disk using slight hand pressure. The portions of the split segments which protrude beyond the face of the grommet and face of the abrasive disk are rounded, relatively non-aggressive in profile, and small in size.

Figure 2:
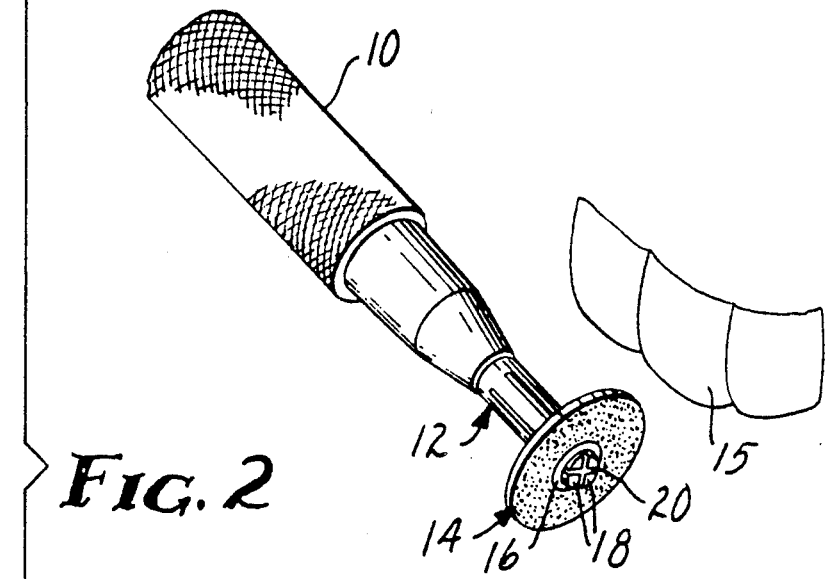
FIG. 2 is an exploded view of the abrasive disk and mandrel shown in FIG. 1.

Referring next to FIG. 2 there is shown, in exploded view, the handpiece, mandrel, and disk of FIG. 1. Handpiece 10, abrasive disk 14, and grommet 16 are as before. The full extent of slots 20 can be seen at the working end of mandrel 12. The contour of split segments 18, the ends of which together form a knob-like terminal portion 26, can also be seen in FIG. 2. Shoulder 22, near the knob-like terminal portion, helps hold the abrasive disk firmly in place and perpendicular to the mandrel when the illustrated parts are assembled. The reverse taper of the knob-like terminal portion also helps hold the abrasive disk firmly in place when the illustrated parts are assembled. The knob-like terminal portion has a flat or flattened end in order to reduce the projection of the mandrel beyond the face of the abrasive disk after the parts are assembled. The presence of a flat or flattened end on the knob-like terminal portion also facilitates the machining of slots 20 in the mandrel. At the driven end of the mandrel can be seen locking flat 27 and retaining groove 28, these two features conforming to one standard driving configuration commonly provided in tools for use in powered rotary dental engines.

Figure 3:
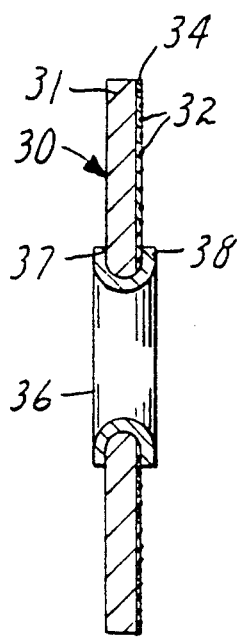
FIG. 3 is a sectional elevation view of an abrasive disk of this invention.

Referring next to FIG. 3 there is shown, in sectional view, abrasive disk 30. The abrasive disk has a backing 31, one surface of which is coated with abrasive grains 32, such grains being held in place by binder 34. Grommet 36 has been made from a brass eyelet having original rim 37 and staked rim 38. The grommet firmly grips the disk backing. In the center of the grommet is an axial, circular hole.

Figure 4:
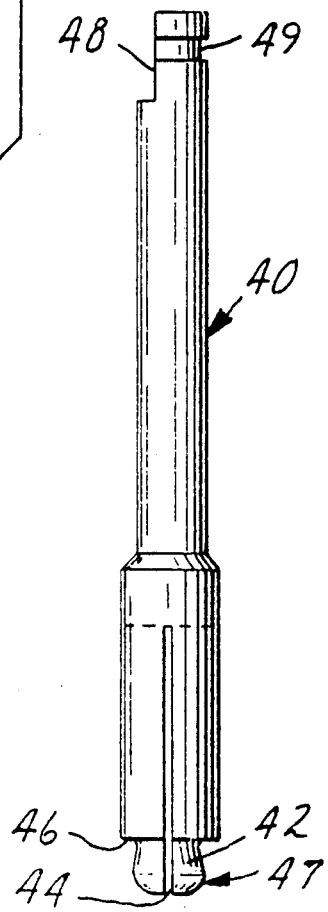
FIG. 4 is an elevation view of a mandrel of this invention.

Referring next to FIG. 4, there is shown in elevation view a mandrel of this invention, designated generally by the numeral 40. The mandrel has split segments 42, slots 44, shoulder 46, and knob-like terminal portion 47 at its working end. The knob-like terminal portion has a slight corner radius near the shoulder, a reverse taper along a part of the knob which will contact a grommet firmly inserted thereon, a flat end, and a rounded beveled edge between the reverse tapered and flattened end portions of the knob. The knob shape shown provides firm engagement of an abrasive disk of this invention, while permitting easy removal and replacement of such disks.

Figure 5:
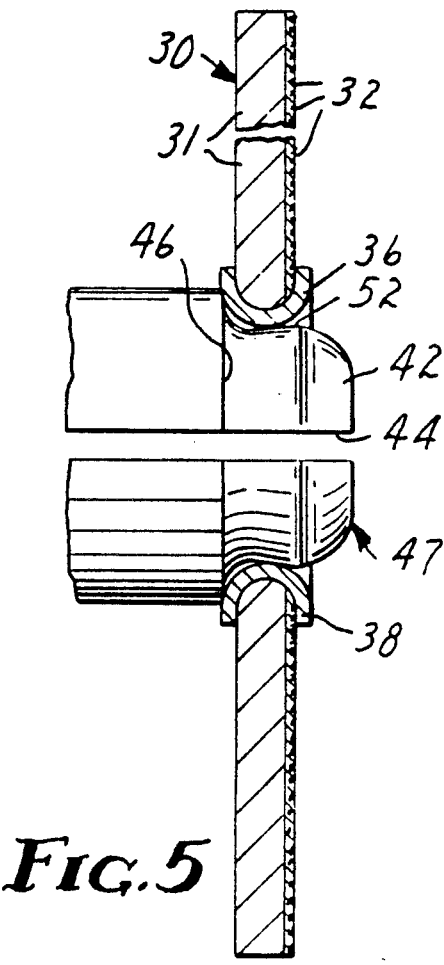
FIG. 5 is an elevation view, partially in section, of the coupling between the disk of FIG. 3 and the mandrel of FIG. 4.

Depicted in FIG. 5 is a close-up view of the abrasive disk of FIG. 3 coupled to the mandrel of FIG. 4. The disk can be easily mounted and demounted on the mandrel, using finger pressure and a "rolling" motion to slide grommet 36 on and off the knob. The disk can be mounted with the abrasive grains facing towards or away from the driving end of the mandrel. Mounting and demounting of the disk is facilitated by slots 44, which compress to allow split segments 42 to flex inward as the grommet slides on or off the knob. When the mandrel is rotated, the split segments flex outward due to spring action or centrifugal force. Tapered sides 52 of the split segments bear against the axial hole in the grommet. The grommet is forced against shoulder 46, thereby providing a slippage-free coupling between the mandrel and disk.

Figure 6:
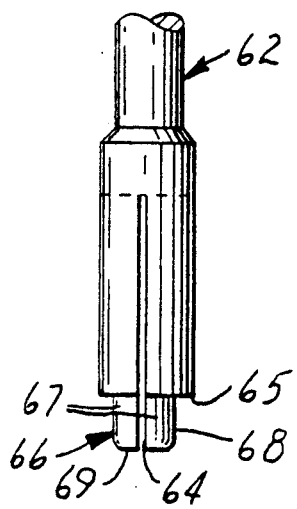
FIG. 6 is an elevation view of the working end of another mandrel of this invention.

Referring next to FIG. 6, there is shown in elevation view the working end of another mandrel of this invention, identified generally by the numeral 62. The mandrel has slots 64 and shoulder 65 which correspond generally to those of the mandrels of FIGS. 1, 2, 4, and 5. However, unlike those mandrels, mandrel 62 is provided with an untapered peg-shaped knob-like portion 67. The knob is formed by split segments 67 provided with generally untapered sides 68 and flattened end 69. The knob has a beveled edge between its sides and its end. When an abrasive disk of this invention is mounted on the mandrel depicted in FIG. 6, the knob-like portion is compressed slightly and assumes a slightly conical shape. However, if the amount of compression of the knob-like portion remains small (e.g., a few micrometers) the mounted disk will remain in place on the mandrel. Under dental grinding conditions, the individual segments of the knob-like portion grip the grommet axially and rotationally with sufficient firmness to enable the disk to be used with the abrasive grains facing either towards or away from the powered rotary dental tool.

Figure 7:
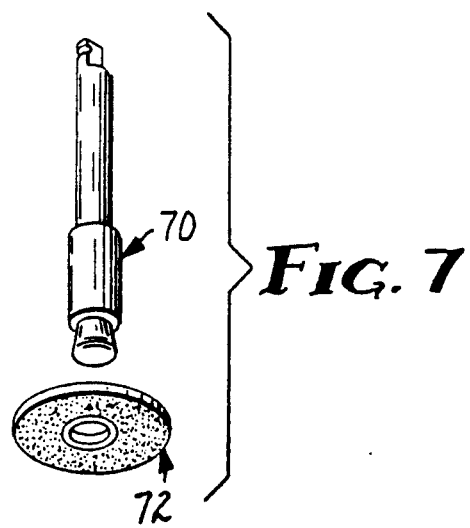
FIG. 7 is an exploded view of an abrasive disk and mandrel of this invention having an unsplit arbor and resilient coupling means between disk and mandrel.

Referring next to FIG. 7, there is shown in exploded view another abrasive disk and mandrel of this invention. Mandrel 70 is provided with an unsplit arbor, and resilient, deformable rubber or plastic coupling means are used to allow removal and replacement of disk 72 with static disengagement and dynamic driving engagement of the disk. Such resilient coupling means are provided by combining a mandrel having a reverse-tapered knob with a rubber or plastic coating on the surface of knob (which coating can deform sufficiently to allow an abrasive disk of this invention to be attached to and detached from the mandrel using hand pressure), or by combining a mandrel having a reverse-tapered knob with a rubber or plastic disk grommet (which grommet can deform sufficiently to allow an abrasive disk of this invention to be attached to and detached from the mandrel using hand pressure).

Figure 8:
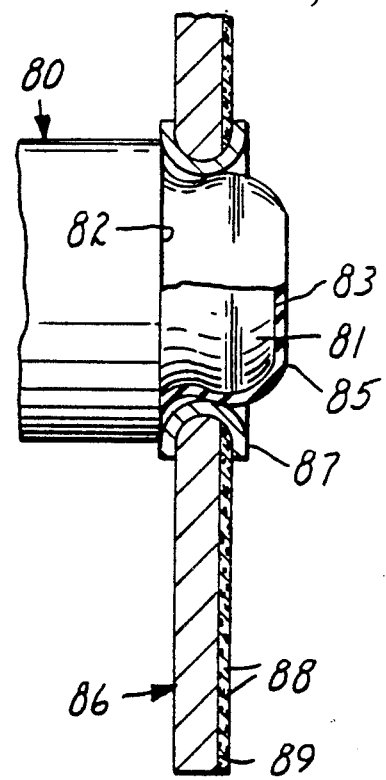
FIG. 8 is a sectional elevation view of one such resilient coupling means.

Depicted in FIG. 8 is a close-up elevation view, partially in section, of one such unsplit arbor and resilient coupling means. Mandrel 80 is provided with knob-like terminal portion 81, shoulder 82, and flattened end 83. The knob-like terminal portion is coated with rubber coating 85. The thickness of the rubber coating and the dimensions of the knob allow abrasive disk 86 to be attached to the mandrel using hand pressure. Along the portion of the coated knob which contacts grommet 87 of the abrasive disk, the knob has a reverse taper. The abrasive disk has a coating of binder 89 and abrasive grains 88. As shown, the abrasive grains face away from the driving end of the mandrel. When the mandrel is at rest, the disk is in static disengagement, that is, it can be rotated using pressure such as finger pressure. When the mandrel is spinning, friction between the rubber coating on the knob and the grommet is sufficient to prevent apparent slippage of the disk during use.

Figure 9:
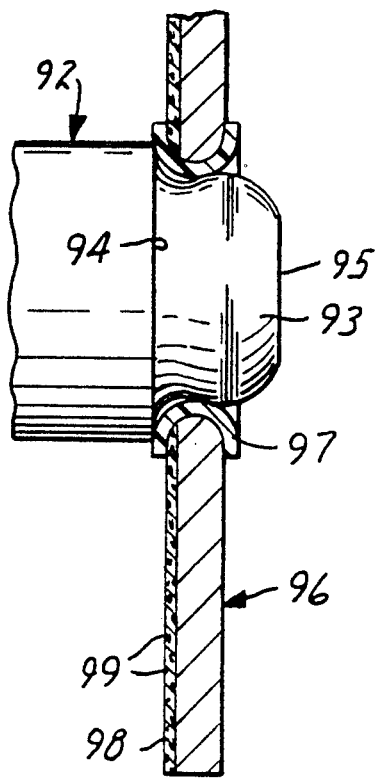
FIG. 9 is a sectional elevation view of another such resilient coupling means.

Depicted in FIG. 9 is a close-up elevation view, partially in section, of another such unsplit arbor and resilient coupling means. Mandrel 92 is provided with knob-like terminal end portion 93, shoulder 94, and flattened end 95. Abrasive disk 96 has a resilient plastic grommet 97 which can deform sufficiently to allow the disk to be attached to the mandrel using hand pressure. Along the portion of the knob which contacts the grommet, the knob has a reverse taper. The abrasive disk has a coating of binder 99 and abrasive grains 98. As shown, the abrasive grains face towards the driving end of the mandrel. When the mandrel is at rest, the disk is in static disengagement. When the mandrel is spinning, friction between the knob and grommet is sufficient to prevent apparent slippage of the disk during use.

A split arbor is the preferred means for providing dynamic driving engagement between disks and mandrels of this invention. If such a split arbor is used, the knob-like terminal portion can be untapered along that part of the knob-like portion's length which will contact a grommet firmly inserted thereon, as viewed before such insertion takes place, that is, the knob-like terminal portion can be essentially peg-like with a cylindrical axial shape when the mandrel is viewed in isolation. Alternatively, and preferably, the knob-like terminal portion can have a reverse taper along a part of the knob-like terminal portion's length which will contact a grommet firmly inserted thereon, as viewed before such insertion takes place, that is, the knob-like terminal portion can be essentially frustum-like with a smaller cross-sectional diameter proximate the shoulder of the mandrel and a generally greater cross-sectional diameter proximate the working end of the mandrel when the mandrel is viewed in isolation. If a corner radius is used between the knob-like terminal portion and the shoulder, then the grommet can optionally contact the mandrel at such corner radius as well as at such part of the knob-like terminal portion which has a reverse taper. Whether untapered or reverse-tapered, such a split arbor is provided with at least one and preferably two or more axial slots which divide the knob-like terminal portion into two or more segments and allow the knob-like terminal portion to be slightly compressed when a grommet is inserted thereon, as well as allowing the knob-like terminal portion to firmly engage the grommet when the mandrel is rotated. When such a split arbor is used, the disk grommet can be made of a rigid or a resilient material.

If an unsplit arbor and resilient rubber or plastic coupling means are used for providing dynamic driving engagement between disk and mandrel, the knob-like terminal portion of the mandrel should have a reverse taper, with "reverse taper" being defined as above. Resilient coupling means which can be used with such an unsplit arbor include the use of a rubber or plastic coating on the knob-like portion of the mandrel having sufficient resilience to permit the disk to be removed from and replaced on the mandrel using hand pressure, and the use of rubber or plastic disk grommets having sufficient resilience to permit the disk to be removed from and replaced on the mandrel using hand pressure.

Whether a split or an unsplit arbor is used, the knob-like terminal portion is desirably beveled proximate the working end of the mandrel. Such a bevel eases attachment of a disk to the mandrel and provides a rounded, non-aggressive end on the working end of the mandrel which minimizes the tendency of the mandrel to strike the surface of a dental restoration or tooth during use. Also, the shoulder of the mandrel preferably has, in axial cross-section, a minimum diameter which is greater than the maximum diameter of the knob-like terminal portion.

Surprisingly, the engagement of the arbor and grommet in the mandrels and disks of this invention is sufficiently firm that such disks can be started from dead stop under load without apparent slippage. Also, the disks and mandrels of this invention can be operated with the abrasive surface of the disks facing either towards or away from the driving end of the mandrel.

The abrasive disks of this invention can be prepared from conventional abrasive materials well known to those skilled in the art. The diameter of such disks can be as small as about 6 millimeters and as large as 22 millimeters or greater. The abrasive disks can be made from rigid or flexible backings coated on one or both faces with standard dental abrasives such as silicon carbide, garnet, cuttle and aluminum oxide, or from rigid or flexible disk materials which are impregnated with such standard abrasives. For example, the disk can be made from cloth or paper backing which is coated with abrasive, or from rubber or phenolic disk materials which are impregnated with abrasive. The abrasive disks of this invention are provided with a hole (preferably circular) through which is inserted a grommet. Preferably the center of the hole is concentric with the center of the abrasive disk. The grommet is fastened to the abrasive disk by stamping, staking, solvent welding, or other means suited to the material from which the grommet is made.

For use with mandrels of this invention having a split arbor and mandrels of this invention having an unsplit arbor in which the knob-like terminal portion is coated with resilient rubber or plastic, the grommet can be plastic such as polystyrene, polypropylene, rubber, or polymethyl methacrylate, or ductile metal such as brass. The grommet is fastened to the disk in a manner which provides firm attachment of the grommet to the disk, such as by solvent welding, cement, or heat-forming for rubber or plastic grommets and swaging or stamping for metal grommets. Brass is a preferred material for use in such grommets. Plated metal grommets made from nickel plated brass eyelets are particularly preferred in order to provide a finished abrasive disk having good resistance to corrosion. Standard brass eyelets such as "Stimson A990" and "USM SE 43" eyelets can be used with flexible paper or plastic backed sheet abrasive and stamped or staked to make abrasive disks having compact, well-formed grommets.

For use with mandrels of this invention having an unsplit arbor and resilient coupling means provided by use of a resilient rubber or plastic disk grommet, the grommet is preferably made of materials such as polypropylene, polystyrene, and polyethylene. Such rubber or plastic grommets should be sufficiently compressible to allow removal and replacement of the disk using hand pressure.

For each of the disk and mandrel combinations described above, the disk grommet and knob-like terminal portion of the mandrel should be sized to provide a slight (e.g., 25 to 50 micrometers) interference fit between the grommet and the part of the knob-like terminal portion which is contacted by the mounted grommet. Such interference fits are measured by determining the point along the length of the knob-like terminal portion at which contact occurs between the grommet of an abrasive disk of this invention and the mandrel of this invention when the abrasive disk is mounted on the mandrel. The cross-sectional diameter of the mandrel (without an abrasive disk mounted thereon) at that point of contact is measured and compared to the inner diameter of the grommet at the point of contact. The difference between the two diameters is the extent of interference fit. The interference fit can be large enough to firmly rotationally lock the disk relative to the mandrel, but such interference fit is preferably small enough to provide static disengagement (as described above) between the disk and mandrel.

The mandrels of the present invention can be any durable, medically acceptable metal. Preferably, the mandrel is made from stainless steel such as a 300 or 400 series stainless steel. Use of stainless steel enables steam autoclaving of the mandrels of this invention without corrosion of the mandrel. A 300 series stainless steel can be employed if a non-magnetic mandrel is desired. Other metals such as bronzes and titanium can also be used in this invention. The driven end of the mandrel (i.e., the end which is inserted in a rotary powered dental engine) is adapted to be mounted in a powered dental tool, that is the driven end should conform to a standard such as American Dental Association (ADA) specification no. 23 for friction fit or latch type tool posts. The working end of the mandrels of this invention (i.e., the end of the mandrel to which an abrasive disk of this invention is detachably mounted) can conform in shape to the shapes shown in the drawing or can be made in other profiles having a shape or taper adapted to lockingly engage the disk grommet of the abrasive disks of this invention, such as wedge-type shapes with a reverse taper. Standard machining practices (including radiusing of edges and avoidance of other stress risers) should be observed when shaping the mandrel. Because the working end of the mandrels of this invention is circular in cross section, such mandrels can be readily formed on automatic screwmaking equipment with fewer machining operations than are required for mandrels (such as the "Moore" mandrel) which have a working end which employs non-circular locking means.

For mandrels of this invention having a split arbor, one or more slots are cut in the working end of the mandrel. The slot or slots can be formed with a slitting saw. A mandrel having two slots of 250 to 350 micrometer width and about 7.5 millimeters depth has been found to give good results for such mandrels, but other numbers of slots or slot dimensions can be used as desired. The slots preferably intersect the central axis of the mandrel, in order to preserve dynamic balance in the mandrel. Also, the depth of the slot or slots preferably extends past the shoulder of the mandrel, in order to provide ample inward compression of the segments of the split arbor when an abrasive disk of this invention is attached to or removed from the mandrel.

Various modifications and alterations of this invention will be apparent to those skilled in the art without departing from the scope and spirit of this invention and the latter should not be restricted to that set forth herein for illustrative purposes.

What is claimed is:

1. A dental abrasive disk having a central aperture and a rigid grommet through said aperture, said grommet having a continuously circular hole whose axis is essentially perpendicular to said disk, said grommet being firmly attached to said disk.

2. A dental abrasive disk according to claim 1, wherein said disk has a diameter between about 6 mm and about 22 mm, and said grommet comprises plastic or ductile metal.

3. A dental abrasive disk according to claim 2, wherein said diameter is less than about 13 mm.

4. A dental abrasive disk according to claim 1, wherein said disk comprises rubber or phenolic, said rubber or phenolic being impregnated with abrasive.

5. A dental abrasive disk comprising a flexible backing, binder, and abrasive, said disk having a central circular aperture and a grommet through said aperture, said grommet containing brass and having a continuously circular central hole whose axis is essentially perpendicular to said disk, said grommet being firmly attached to said disk.

* * * * *